(12) United States Patent
Van Muiswinkel

(10) Patent No.: US 9,092,860 B2
(45) Date of Patent: Jul. 28, 2015

(54) HANDLING OF DATASETS

(75) Inventor: Arianne Van Muiswinkel, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1995 days.

(21) Appl. No.: 11/721,183

(22) PCT Filed: Dec. 14, 2005

(86) PCT No.: PCT/IB2005/054234
§ 371 (c)(1),
(2), (4) Date: Jun. 8, 2007

(87) PCT Pub. No.: WO2006/067685
PCT Pub. Date: Jun. 29, 2006

(65) Prior Publication Data
US 2009/0240706 A1    Sep. 24, 2009

(30) Foreign Application Priority Data
Dec. 21, 2004    (EP) .................................... 04106760

(51) Int. Cl.
G06F 17/00 (2006.01)
G06F 7/00 (2006.01)
G06T 7/00 (2006.01)
G06F 19/26 (2011.01)

(52) U.S. Cl.
CPC .............. G06T 7/0028 (2013.01); G06F 19/26 (2013.01); *G06T 2207/30101* (2013.01)

(58) Field of Classification Search
CPC ........ G06F 19/321; G06F 19/26; G06Q 50/24
USPC ................................... 707/737, 741
See application file for complete search history.

(56) References Cited

U.S. PATENT DOCUMENTS

| 5,555,409 | A | * | 9/1996 | Leenstra et al. ..................... 1/1 |
| 5,720,291 | A | * | 2/1998 | Schwartz ....................... 600/456 |
| 5,987,345 | A | * | 11/1999 | Engelmann et al. .......... 600/407 |
| 6,081,267 | A | * | 6/2000 | Stockham et al. ............ 715/788 |
| 6,826,297 | B2 | | 11/2004 | Saito |

(Continued)

FOREIGN PATENT DOCUMENTS

| JP | 05285116 A | 11/1993 |
| JP | 06000170 A | 1/1994 |

(Continued)

OTHER PUBLICATIONS

Analyzedirect: "Analyze 5.0 Manual"; 2004; Chapter 15—Registration.

(Continued)

*Primary Examiner* — Pavan Mamillapalli

(57) ABSTRACT

A data handling system for handling multiple datasets is provided with an access module for accessing datasets of several categories and a connection module to link datasets in the respective categories. From a region of interest in one anatomical image a link is provided to the corresponding region of interest in other types of images and/or other types of data, such as a time intensity curve for that region of interest. Also the propagation of the region of interest in one image, such as an anatomical image, through a temporal succession of images may constitute links through an image series.

16 Claims, 1 Drawing Sheet

(56) References Cited

U.S. PATENT DOCUMENTS

| | | | |
|---|---|---|---|
| 7,190,163 B2* | 3/2007 | Rajagopalan et al. | 324/309 |
| 8,050,938 B1* | 11/2011 | Green et al. | 705/2 |
| 2001/0029509 A1* | 10/2001 | Smith et al. | 707/104.1 |
| 2003/0013951 A1 | 1/2003 | Stefanescu | |
| 2005/0105775 A1* | 5/2005 | Luo et al. | 382/115 |
| 2005/0267371 A1 | 12/2005 | Ogasawara | |
| 2005/0271271 A1 | 12/2005 | Noble et al. | |
| 2006/0188134 A1* | 8/2006 | Quist | 382/128 |
| 2008/0126982 A1* | 5/2008 | Sadikali et al. | 715/810 |
| 2013/0208955 A1* | 8/2013 | Zhao et al. | 382/128 |

FOREIGN PATENT DOCUMENTS

| | | |
|---|---|---|
| JP | 2004202142 A | 7/2004 |
| JP | 2004351050 A | 12/2004 |
| WO | 0227712 A1 | 4/2002 |
| WO | 03107275 A2 | 12/2003 |
| WO | 2004027712 A2 | 4/2004 |
| WO | 2004086972 A2 | 10/2004 |

OTHER PUBLICATIONS

Guyon, J-P; Vetot: Volume Estimation and Tracking Over Time; 2004; Section 3—Registration. http://web.archive.org/web/.

Maintz, J.B.A., et al.; A Survey of Medical Image Registration; 1998; Medical Image Analysis; 2(1)1-37.

Samtaney, R., et al.; Visualizing Features and Tracking Their Evolution; 1994; Computer USA; 27(7)20-27.

Computer Aided Diagnosis and Display Lab, 2011.

* cited by examiner

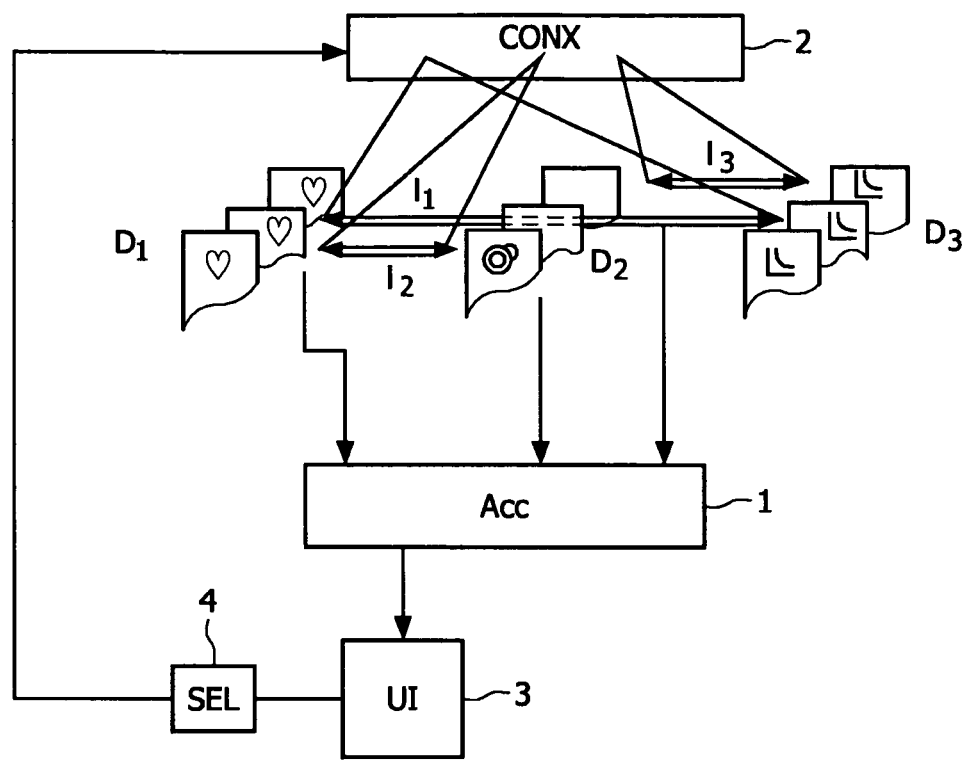

HANDLING OF DATASETS

The invention pertains to a data handling system.

Such a data handling system is known from the international application WO 2002/027712.

The known data handling system is arranged to operate on data sets that concern series of 2D or 3D images. The data handling involves transformation and segmentation of the images. Each separate transformation is based on a fitting operation between two images of a series of images. When a segmentation has been performed on one (the first) image, that segmentation on the first image of the series is modified on the basis of the transformation that fits or e.g. warps the first image to a next image of the series. The modified transformation is then applied to that next image of the series. This allows for easy comparison among images of the series without much human intervention.

An object of the invention is to provide a data handling system that has the capability to handle datasets more efficiently, in particular when the datasets represent a wide variety of data.

The present invention notably aims at datasets of various different types. For example in medical diagnostic magnetic resonance examination several different series of data are acquired and from the data that are acquired in the form of magnetic resonance signals there are constructed additional datasets. For example, in a functional brain examination based on magnetic resonance there is formed an anatomical survey image, several high-resolution anatomical images, series of diffusion weighted images and perfusion images. Additional data series, such as time intensity curves, are derived from the diffusion weighted images as well as from the perfusion images. All of these data may be involved in a clinical analysis. This clinical analysis includes viewing of the images within a series and comparing series with each other. The clinical analysis may also involve examining a time intensity curve that pertains to a particular anatomical feature. Thus, next to anatomical structure that is represented in the images physiological functional information represented by the time intensity curves are employed in the clinical analysis. The known data handling system only provides for an automatic proliferation of a segmentation scheme from one image to the next within a series of images.

The object of the present invention is achieved by the data handling system of the invention which comprises
  an access module for accessing datasets of several categories
  a connection module to link datasets in the respective categories.

The invention is based on the insight that datasets of different categories can be linked. That is, relationships can be established between particular information parts in the datasets. The data handling system of the invention is in particular used to handle medically diagnostic datasets, such as anatomical images, functional images or datasets relating to physiological quantities. For example when for example one dataset is an anatomical image a particular information part in the dataset such as a region of interest can be identified. For example a second dataset relates to a time intensity curve. The relationship established represents the time intensity curve for the identified region of interest. According to one aspect of the invention the information parts that have the same origin in the object to be examined, such as the patient to be examined, notably relate to the same portion of the anatomy constitute the basis for the respective datasets to be linked. The linking of the datasets of different categories facilitates navigation through the categories of datasets. In particular, for example the user needs only to indicate a region of interest in one anatomical images and the invention automatically provides the linked portion of datasets in either different categories but also may provide the linked portion in other datasets in the same category. Thus, from a region of interest in one anatomical image a link is provided to the corresponding region of interest in other types of images and/or other types of data, such as a time intensity curve for that region of interest. Also the propagation of the region of interest in one image, such as an anatomical image, through a temporal succession of images may constitute links through an image series.

These and other aspects of the invention will be further elaborated with reference to the embodiments defined in the dependent Claims.

According to a further aspect of the invention, datasets of respective categories form ordered successions of datasets. For example, such an ordered succession is formed by a time series of images. For respective categories such as magnetic resonance images of different contrast types, there occur individual ordered successions of these magnetic resonance images. According to the invention, the connection module is also arranged to link an ordered succession in one category to an ordered succession in another category. In particular, time series of images different contrast may be linked to each other. Or, a time intensity curve may be linked to a time series of images.

According to a further aspect of the invention the linking of datasets is made on the basis of corresponding features. That is, datasets are linked through information parts that pertain to the same origin in the object to be examined.

According to a further aspect of the invention, a selection module is provided to select a feature in one of the dataset in one particular category. For example, the feature selected is a region of interest in an anatomical image. This selected feature is then employed by the connection module to establish links to other datasets in other and/or the same category. That is when linking to other categories, for example the region of interest may be linked to corresponding regions of interest in images of other contrast types, or to time intensity curves for the selected region of interest. When, linking within a category, for example the selected region of interest in one image is propagated through the ordered succession of a time series of images. The selection module may be operated on the basis of user input. Thus, the user may indicate the region of interest to be selected an input the selection to the selection module, which then carries out the selection in the datasets.

These and other aspects of the invention will be elucidated with reference to the embodiments described hereinafter and with reference to the accompanying drawing wherein FIG. 1 shows a diagrammatic representation of the data handling system of the invention.

FIG. 1 shows a diagrammatic representation of the data handling system of the invention. The data handling system's access module 1 has access to various datasets in various categories (D1 . . . D3). For example dataset D1 concerns a succession of anatomic cardiac magnetic resonance images, dataset D2 concerns a succession of cardiac perfusion images and dataset D3 concerns a succession of time intensity curves. The access module can access individual images from these datasets, but also entire series can be accessed. The connection module 2 arranges links ($l_1, \ldots l_3$) between the datasets. The links may occur between single images or data parts of datasets, between one image in one dataset and a multitude of images or data parts in one or more the same or other datasets, among multitudes of images or data parts in different datasets or between a multitude of images or data parts in the same dataset. The access module is enabled on the basis of the links established by the connection module to provide the linked data to the user interface 3. Accordingly, all linked data, e.g. anatomical images, functional images, time intensity curves that are related as represented by them being linked are made available to the user.

Moreover, the user interface 3 is coupled to the selection unit. The selection module 4 is controlled by a selection signal supplied by the user interface 3 to select datasets from the various categories to be linked by the connection module 2. The selection signal may be generated, for example on the basis of user input or automatically. The user input is for example a selected region of interest in one of the images shown on the user interface. The selection module then causes the connection unit to establish links to datasets in the various categories that pertain to the same region of interest. In an automatic mode, the selection signal may be generated e.g. by automatic identification of a particular feature in one of the images.

The invention claimed is:

1. A medical diagnostic data handling system, comprising:
one or more memories which store a plurality of medically diagnostic datasets;
a user interface device on which a user views medically diagnostic information of a selected patient and on which the user inputs a patient selection and an anatomical region of interest selection;
a connection module which searches through the one or more memories storing medically diagnostic datasets and establishes links between parts of the medically diagnostic information in the plurality of medically diagnostic data sets relating to the patient selection and the anatomical region selection from the user interface device, wherein the plurality of medically diagnostic datasets includes anatomical and functional image datasets which contain anatomical and functional images generated at different times,
and further wherein the connection module links the selected anatomical regions of interest together in a temporally ordered succession, wherein the connection module is configured to link an ordered succession in one region of interest to an ordered succession in another region of interest; and
an access module which accesses the plurality of medically diagnostic datasets based on the links established by the connection module to retrieve the parts of medically diagnostic information relating to the patient selection and the anatomical region of interest selection from the user interface device, and forwards the retrieved parts of the medically diagnostic information to the user interface device for display.

2. The medical diagnostic data handling system as claimed in claim 1, wherein the plurality of medically diagnostic datasets includes an anatomical image dataset which stores anatomical images of a plurality of patients.

3. The medical diagnostic data handling system as claimed in claim 2, wherein the medically diagnostic datasets includes a physiological quantity dataset which stores physiological quantities of the patients.

4. The medical diagnostic data handling system as claimed in claim 3, wherein the physiological quantities include time intensity curves.

5. The medical diagnostic data handling system as claimed in claim 3, wherein the plurality of medically diagnostic datasets includes a functional image dataset which stores functional images of the patients.

6. The medical diagnostic data handling system as claimed in claim 3, wherein the plurality of medically diagnostic datasets includes contrast enhanced images with different contrasts.

7. A medical diagnostic data handling system, comprising:
one or more memories which store a plurality of medically diagnostic datasets;
a user interface including a display device on which a user views medically diagnostic information of a selected patient and a user input device on which the user inputs a patient selection and an anatomical region of interest selection;
one or more modules or processors configured to:
receive the patient selection and the anatomical region of interest selection and establish links between parts of the medically diagnostic information in the plurality of medically diagnostic datasets stored in the one or more memories corresponding to the patient selection and the anatomical region selection by searching through the one or more memories storing medically diagnostic datasets,
and wherein the one or more modules or processors are further configured to link a temporally ordered succession of anatomical and function images which correspond to the patient selection and a first anatomical region of interest selection to an ordered succession of a second anatomical region of interest selection,
access the plurality of medically diagnostic datasets in the one or more memories based on the established links to retrieve the linked parts of medically diagnostic information corresponding to the patient selection and the anatomical region of interest selection, and
control the display device to display the retrieved linked parts of the medically diagnostic information corresponding to the patient selection and the anatomical region of interest selection.

8. The medical diagnostic data handling system as claimed in claim 7, wherein the plurality of medically diagnostic datasets stored in the one or more memories includes an anatomical image dataset which stores anatomical images of a plurality of patients.

9. The medical diagnostic data handling system as claimed in claim 8, wherein the medically diagnostic datasets stored in the one or more memories includes a physiological quantity dataset which stores physiological quantities of the patients.

10. The medical diagnostic data handling system as claimed in claim 9, wherein the physiological quantities include time intensity curves.

11. The medical diagnostic data handling system as claimed in claim 9, wherein the plurality of medically diagnostic datasets stored in the one or more memories includes a functional image dataset which stores functional images of the patients.

12. The medical diagnostic data handling system as claimed in claim 9, wherein the plurality of medically diagnostic dataset stored in the one or more memories includes contrast enhanced images with different contrasts.

13. The medical diagnostic data handling system as claimed in claim 7, wherein the one or more memories receive and store anatomical image datasets and functional image datasets which contain anatomical and functional images generated at different times and wherein the one or more modules or processors are further configured to:
link anatomical regions of the anatomical images and the functional images which correspond to the patient selection and the anatomical region of interest selection.

14. A medical diagnostic data handling system comprising:
one or more memories which store at least a first category dataset and a second category dataset, the first category dataset including medical diagnostic images, the medical diagnostic images being identified by patient and by anatomical region, the second dataset including physiological data identified by patient;
a user interface device on which a user selects a patient and an anatomical region and on which the user views medical information of the selected patient;
one or more modules or processors configured to:
  search through the one or more memories and establish links among parts of the medically diagnostic images of the selected anatomical region of the selected patient and the physiological data relating to the selected anatomical region of the selected patient, wherein the medically diagnostic images are generated at different times,
    and further wherein the one or more modules or processors links the selected anatomical regions of interest together in a temporally ordered succession, wherein the one or more modules or processors are further configured to link an ordered succession in the selected anatomical region to an ordered succession in another anatomical region;
  access the linked parts of medically diagnostic images and physiological data based on the established links to retrieve the parts of medically diagnostic images and the physiological data corresponding to the selected patient and the selected anatomical region from the user interface device, and
  forward the retrieved linked parts of the medically diagnostic images and physiological data to the user interface device for display.

15. The medical diagnostic data handling system as claimed in claim 14, wherein the medical diagnostic images include:
  anatomical images,
  functional images,
  diffusion weighted images, and
  perfusion images.

16. The medical diagnostic data handling system as claimed in claim 15, wherein the physiological quantities include time intensity curves and the one or more modules or processors are further configured to:
  link the time intensity curves, parts of the anatomical images, and parts of at least one of the diffusion weighted images and the perfusion images which correspond to the selected patient and the selected anatomical region; and
  control the user interface to display the linked time intensity curves and the parts of the images.

* * * * *